United States Patent
Matsuzawa et al.

(10) Patent No.: US 8,287,900 B2
(45) Date of Patent: Oct. 16, 2012

(54) MEDICATED PATCH COMPRISING 5-METHYL-1-PHENYL-2-(1H)-PYRIDONE

(75) Inventors: Takayasu Matsuzawa, Toyama (JP); Tamaki Horiuchi, Toyoma (JP); Seijiro Yama, Toyoma (JP); Tetsukazu Hamamoto, Toyama (JP); Sunao Takeuchi, Toyama (JP); Daisuke Ichimatsu, Toyama (JP)

(73) Assignees: Lead Chemical Co., Ltd., Toyama-Shi (JP); Shionogi & Co., Ltd., Osaka-Shi (JP)

(*) Notice: Subject to any disclaimer, the term of this patent is extended or adjusted under 35 U.S.C. 154(b) by 266 days.

(21) Appl. No.: 12/451,646

(22) PCT Filed: May 26, 2008

(86) PCT No.: PCT/JP2008/059672
§ 371 (c)(1),
(2), (4) Date: Jan. 4, 2010

(87) PCT Pub. No.: WO2008/146796
PCT Pub. Date: Dec. 4, 2008

(65) Prior Publication Data
US 2010/0119584 A1 May 13, 2010

(30) Foreign Application Priority Data
May 25, 2007 (JP) ................. 2007-139653

(51) Int. Cl.
*A61L 15/16* (2006.01)
*A61F 13/00* (2006.01)
*A61K 9/70* (2006.01)
*A61K 9/14* (2006.01)
*A61L 15/00* (2006.01)

(52) U.S. Cl. ........ 424/447; 424/443; 424/444; 424/445; 424/485; 424/486; 514/345

(58) Field of Classification Search ................. 424/447, 424/443, 444, 445, 485, 486; 514/345
See application file for complete search history.

(56) References Cited

U.S. PATENT DOCUMENTS

| | | | | |
|---|---|---|---|---|
| 4,695,465 | A * | 9/1987 | Kigasawa et al. | 424/449 |
| 5,167,649 | A * | 12/1992 | Zook | 604/307 |
| 6,492,395 | B1 * | 12/2002 | Scheiwe et al. | 514/327 |
| 7,605,173 | B2 | 10/2009 | Seth | |

FOREIGN PATENT DOCUMENTS

| | | |
|---|---|---|
| JP | A-2004-203795 | 7/2004 |
| JP | A-2006-298774 | 11/2006 |
| WO | WO 02/060446 A1 | 8/2002 |
| WO | WO 2004/073680 A1 | 9/2004 |
| WO | WO 2004/073713 A1 | 9/2004 |

OTHER PUBLICATIONS

International Search Report mailed on Jul. 15, 2008 in corresponding International Application No. PCT/JP2008/059672 (with translation).

* cited by examiner

*Primary Examiner* — Johann Richter
*Assistant Examiner* — Jane C Oswecki
(74) *Attorney, Agent, or Firm* — Oliff & Berridge, PLC

(57) ABSTRACT

There is provided a medicated patch including 5-methyl-1-phenyl-2-(1H)-pyridone. A medicated patch comprising a percutaneously absorbable preparation layer, wherein the percutaneously absorbable preparation layer includes 5-methyl-1-phenyl-2-(1H)-pyridone or a pharmaceutically acceptable salt thereof as an active component, a dissolving agent and an aqueous base material (or a rubber-type base material), and the active component is contained in an amount of 0.1 to 30 mass % relative to the total amount of the percutaneously absorbable preparation layer.

6 Claims, 2 Drawing Sheets

US 8,287,900 B2

MEDICATED PATCH COMPRISING 5-METHYL-1-PHENYL-2-(1H)-PYRIDONE

TECHNICAL FIELD

The present invention relates to a medicated patch including a percutaneously absorbable preparation layer, which is effective for the prophylaxis and treatment of skin diseases such as hyperplastic scar, keloid, contact dermatitis, infectious verruca (wart), pustulosis palmaris et plantaris or fibrous skin disease. More specifically, the present invention relates to a medicated patch including 5-methyl-1-phenyl-2-(1H)-pyridone (generic name: Pirfenidone) or a pharmaceutically acceptable salt thereof as an active component.

BACKGROUND ART

It is known that 5-methyl-1-phenyl-2-(1H)-pyridone is useful for the prophylaxis and treatment of fibrous diseases including pulmonary fibrosis, fibrosing hypertrophy of prostate and nephrosclerosis.

Furthermore, until now, a tablet including 5-methyl-1-phenyl-2-(1H)-pyridone as a base component has been suggested as a drug for the treatment of pulmonary fibrosis (see Patent Document 1). Moreover, a solution-type pharmaceutical composition has been suggested as a drug having other for the treatment of fibrous skin diseases (see Patent Document 2).

However, a medicated patch using 5-methyl-1-phenyl-2-(1H)-pyridone or a pharmaceutically acceptable salt thereof as an active component for the prophylaxis or treatment of skin diseases, which is excellent in skin permeability, sustentation of medicinal effect, and the like, and exhibits fine adhesion, flexibility, aggregability and the like, is not known.
Patent Document 1: WO2002/060446
Patent Document 2: JP-A No. 2004-203795

DISCLOSURE OF THE INVENTION

Problem to be Solved by the Invention

The present invention aims at solving the above-mentioned problem, and the object thereof is to provide a medicated patch including 5-methyl-1-phenyl-2-(1H)-pyridone which provides fine skin permeability of the active component (5-methyl-1-phenyl-2-(1H)-pyridone or a pharmaceutically acceptable salt thereof), sustentation of medicinal effect, adhesion, flexibility and/or aggregability.

Means for Solving the Problem

The present inventors have done intensive studies to achieve the above-mentioned purpose, and consequently found that 1) solubility of 5-methyl-1-phenyl-2-(1H)-pyridone to an aqueous base material is improved by selecting, as a dissolving agent, peppermint oil, oleyl alcohol, isopropanol, propylene glycol, butylene glycol, N-methyl-pyrrolidone, diethylene glycol monoethyl ether, triacetine, glycerin, crotamiton, macrogol, isopropyl myristate, glycerin triethyl hexanoate, diisopropyl sebacate, diethyl sebacate, diisopropyl adipate, triethyl citrate, ethylene glycol salicylate, propylene carbonate and medium-chain fatty acid triglycerides from various dissolving agents used in aqueous base materials, whereby 5-methyl-1-phenyl-2-(1H)-pyridone in an amount sufficient for exhibiting medicinal effect can be retained in a base material, and 2) an aqueous-type medicated patch including 5-methyl-1-phenyl-2-(1H)-pyridone having preferable adhesion, flexibility and/or aggregability for medicated patches may be produced by specifying the composition of the aqueous base material in which the dissolving agent has been incorporated as a water-soluble polymer in an amount of 1 to 20 mass %, a crosslinking agent in an amount of 0.01 to 20 mass %, a polyvalent alcohol in an amount of 10 to 80 mass % and water in an amount of 5 to 80 mass % relative to the total amount of the percutaneously absorbable preparation layer.

The present inventors have also found that an oil-based medicated patch including 5-methyl-1-phenyl-2-(1H)-pyridone having the above-mentioned effects may be produced by 1) selecting peppermint oil, oleyl alcohol, isopropanol, propylene glycol, butylene glycol, N-methyl-pyrrolidone, diethylene glycol monoethyl ether, triacetine, glycerin, crotamiton, macrogol, isopropyl myristate, glycerin triethyl hexanoate, diisopropyl sebacate, diethyl sebacate, diisopropyl adipate, triethyl citrate, ethylene glycol salicylate and propylene carbonate as a dissolving agent from various dissolving agents used in rubber base materials, and by 2) specifying the composition of the rubber-type base material in which the dissolving agent has been incorporated as a rubber-type polymer in an amount of 10 to 50 mass %, a plasticizer in an amount of 10 to 50 mass % and a tackifier in an amount of 5 to 50 mass %, and completed the present invention.

Namely, the first aspect of the present invention relates to a medicated patch including a percutaneously absorbable preparation layer, wherein the percutaneously absorbable preparation layer includes 5-methyl-1-phenyl-2-(1H)-pyridone or a pharmaceutically acceptable salt thereof as an active component, a dissolving agent and an aqueous base material, wherein the active component is contained in an amount of 0.1 to 30 mass % relative to the total amount of the percutaneously absorbable preparation layer.

The second aspect of the present invention relates to the medicated patch according to the first aspect, wherein the dissolving agent is selected from the group consisting of peppermint oil, oleyl alcohol, isopropanol, propylene glycol, butylene glycol, N-methyl-pyrrolidone, diethylene glycol monoethyl ether, triacetine, glycerin, crotamiton, macrogol, isopropyl myristate, glycerin triethyl hexanoate, diisopropyl sebacate, diethyl sebacate, diisopropyl adipate, triethyl citrate, ethylene glycol salicylate, propylene carbonate and medium-chain fatty acid triglycerides.

The third aspect of the present invention relates to the medicated patch according to the first or second aspect, wherein the aqueous base material includes a water-soluble polymer in an amount of 1 to 20 mass %, a crosslinking agent in an amount of 0.01 to 20 mass %, a polyvalent alcohol in an amount of 10 to 80 mass % and water in an amount of 5 to 80 mass % relative to the total amount of the percutaneously absorbable preparation layer.

The fourth aspect of the present invention relates to a medicated patch including a percutaneously absorbable preparation layer, wherein the percutaneously absorbable preparation layer includes 5-methyl-1-phenyl-2-(1H)-pyridone or a pharmaceutically acceptable salt thereof as an active component, a dissolving agent and a rubber-type base material, wherein the active component is contained in an amount of 0.1 to 30 mass % relative to the total amount of the percutaneously absorbable preparation layer.

The fifth aspect of the present invention relates to the medicated patch according to the fourth aspect, wherein the dissolving agent is selected from the group consisting of peppermint oil, oleyl alcohol, isopropanol, propylene glycol, butylene glycol, N-methyl-pyrrolidone, diethylene glycol monoethyl ether, triacetine, glycerin, crotamiton and macrogol, isopropyl myristate, glycerin triethyl hexanoate, diisopropyl sebacate, diethyl sebacate, diisopropyl adipate, triethyl citrate, ethylene glycol salicylate and propylene carbonate.

The sixth aspect of the present invention relates to the fourth or fifth aspect, wherein the rubber-type base material includes a rubber-type polymer in an amount of 10 to 50 mass %, a plasticizer in an amount of 10 to 50 mass % and a tackifier in an amount of 5 to 50 mass % relative to the total amount of the percutaneously absorbable preparation layer.

Effects of the Invention

In the medicated patch including 5-methyl-1-phenyl-2-(1H)-pyridone of the present invention, the solubility of the active component (5-methyl-1-phenyl-2-(1H)-pyridone or a pharmaceutically acceptable salt thereof) in the base material is improved by selecting and using a suitable dissolving agent depending on the base material (an aqueous base material or a rubber-type base material) to be used. Therefore, the skin permeability of the active component is high, the active component may be retained in an amount sufficient for exhibiting medicinal effect in the base material, and the medicinal effect is sustained for a long time period.

Furthermore, the medicated patch including 5-methyl-1-phenyl-2-(1H)-pyridone of the present invention has preferable adhesion, flexibility and/or aggregability for medicated patches by selecting a suitable dissolving agent according to the base material, and combining the dissolving agent with a specific base material component.

Therefore, skin diseases such as hypertrophic scar, keloid, contact dermatitis, infectious verruca (wart), pustulosis palmaris et plantaris or fibrous skin disease may be effectively prevented or treated by using the medicated patch including 5-methyl-1-phenyl-2-(1H)-pyridone of the present invention.

Furthermore, the medicated patch including 5-methyl-1-phenyl-2-(1H)-pyridone of the present invention may locally administer a medicinally active component, i.e., 5-methyl-1-phenyl-2-(1H)-pyridone to an affected site by adhering the medicated patch, and the medicinally active component directly permeates the affected site on which the medicated patch is adhered.

Therefore, the medicated patch including 5-methyl-1-phenyl-2-(1H)-pyridone of the present invention can effectively prevent and treat skin diseases without causing side effects such as photosensitivity since the drug is not systemically diffused.

BEST MODE FOR CARRYING OUT THE INVENTION

The active component for the medicated patch of the present invention is 5-methyl-1-phenyl-2-(1H)-pyridone.

Alternatively, the active component 5-methyl-1-phenyl-2-(1H)-pyridone may be a pharmaceutically acceptable salt thereof.

Examples of such salt may include acid addition salts with an acid such as hydrochloric acid, sulfuric acid, phosphoric acid, paratoluenesulfonic acid or methanesulfonic acid, or alkali salts including sodium salts and potassium salts.

Although the amount to be incorporated of the active component in the medicated patch of the present invention differs according to the formulation, it is desirable to incorporate the active component by an amount of about 0.1 to 30 mass %, preferably about 0.5 to 20 mass %, specifically about 0.5 to 10 mass % relative to the total amount of the percutaneously absorbable preparation layer.

The dissolving agent used in the medicated patch of the present invention differs according to the base material (an aqueous base material or a rubber-type base material) to which the active component 5-methyl-1-phenyl-2-(1H)-pyridone is to be dissolved or suspended.

The dissolving agent is selected from the group consisting of peppermint oil, oleyl alcohol, isopropanol, propylene glycol, butylene glycol, N-methyl-pyrrolidone, diethylene glycol monoethyl ether, triacetine, glycerin, crotamiton, macrogol, isopropyl myristate, glycerin triethyl hexanoate, diisopropyl sebacate, diethyl sebacate, diisopropyl adipate, triethyl citrate, ethylene glycol salicylate, propylene carbonate and medium-chain fatty acid triglycerides when an aqueous base material is used as the base material, or selected from the group consisting of peppermint oil, oleyl alcohol, isopropanol, propylene glycol, butylene glycol, N-methyl-pyrrolidone, diethylene glycol monoethyl ether, triacetine, glycerin, crotamiton, macrogol, isopropyl myristate, glycerin triethyl hexanoate, diisopropyl sebacate, diethyl sebacate, diisopropyl adipate, triethyl citrate, ethylene glycol salicylate and propylene carbonate when a rubber-type base material is used as the base material.

These dissolving agents used according to the base material may be used by solely one kind, or as a suitable mixture of two or more kinds. The amount of these dissolving agents to be incorporated is about 0.1 to 20 mass % relative to the total amount of the percutaneously absorbable preparation layer.

The base material in the medicated patch of the present invention is preferably an aqueous base material or a rubber-type base material. As the aqueous base material, for example, a mixture of component 1): a water-soluble polymer, component 2): a crosslinking agent, component 3): a polyvalent alcohol and water may be used, and as the rubber-type base material, for example, a mixture of component 4): a rubber-type polymer, component 5): a plasticizer and component 6): a tackifier may be used.

Examples of the water-soluble polymer of component 1) which may be used may include, but are not limited to, polyacrylic acid, polyacrylic acid salts, partially neutralized products of polyacrylic acid, polyacrylamide, polyethyleneimine, polyvinyl alcohol, polyvinyl pyrrolidone, carboxyvinyl polymer, methyl cellulose, carboxymethyl cellulose, sodium carboxymethyl cellulose, hydroxyethyl cellulose, acrylic acid starch, vinyl ethyl acetate, gelatin, starch, Eudragit, alginic acid, sodium alginate and tragacanth. These water-soluble polymers may be used by solely one kind, or as a suitable mixture of two or more kinds.

The amount of these water-soluble polymers to be incorporated is about 1 to 20 mass %, preferably about 5 to 15 mass % relative to the total amount of the percutaneously absorbable preparation layer.

As the crosslinking agent of component 2), for example, a salt which generates a bivalent or trivalent metal ion when dissolved in water may be used. Examples of such crosslinking agent may include, but are not limited to, hydroxides including aluminum hydroxide and aluminum magnesium hydroxide, or normal salts of inorganic acids or organic acids, or basic salts thereof including aluminum chloride, aluminum sulfate, dihydroxyaluminum aminoacetate, kaolin, aluminum stearate, magnesium hydroxide, magnesium chloride, magnesium sulfate, double salts including aluminum alum, as well as aluminates such as sodium aluminate, inorganic aluminum complex salts and organic aluminum chelate compounds, synthetic hydrotalcite, magnesium metasilicate aluminate, magnesium silicate aluminate, aluminum nitrate, aluminum sulfate, EDTA-aluminum, aluminum allantoinate, aluminum acetate and aluminum glycinal. These crosslinking agents may be used by solely one kind, or as a suitable mixture of two or more kinds. The amount of these crosslinking agents to be incorporated is 0.01 to 20 mass %, preferably 0.02 to 5 mass % relative to the total amount of the percutaneously absorbable preparation layer.

The above-mentioned salts which generate a bivalent or trivalent metal ion as the crosslinking agent may be water-soluble or poorly-water soluble. When a poorly-water soluble aluminum compound is used as the above-mentioned crosslinking agent, a reaction rate-adjusting agent may be added to a reaction system in which gellation is to be performed, and the reaction rate of gellation may be increased by adding an acid. Specifically, the gellation reaction is significantly accelerated by adding an organic acid including a hydroxy group or a salt thereof as a salt. Examples of the rate-adjusting agent which can be utilized for these crosslinking reactions include, but are not limited to, organic acids, organic acid salts, organic bases and the like having ability of forming a chelate or ability of coordinating to metal ion including citric acid, lactic acid, tartaric acid, gluconic acid, glycolic acid, malic acid, fumaric acid, metasulfonic acid, maleic acid, acetic acid, EDTA-2 sodium, urea, triethylamine and ammonia, and inorganic acids and the like including hydrochloric acid, phosphoric acid, sulfuric acid, nitric acid and hydrobromic acid.

Examples of the polyvalent alcohol of component 3) may include, but are not limited to, ethylene glycol, trimethylene glycol, 1,3-butanediol, ethylene glycol monobutyl ether, triethylene glycol, 1,4-butanediol, glycerin, trioxy isobutane, Erythrite, Pentaerythrite, xylite, adonite, allodulcit, sorbitol, sorbit liquid, mannitol and polyethylene glycol. These polyvalent alcohols may be used by solely one kind, or as a suitable mixture of two or more kinds. The amount of these polyvalent alcohols to be incorporated is about 10 to 80 mass %, preferably about 10 to 60 mass % relative to the total amount of the percutaneously absorbable preparation layer.

Furthermore, the aqueous base material includes water, and the amount thereof to be incorporated is about 5 to 80 mass % relative to the total amount of the percutaneously absorbable preparation layer.

It is preferable that the aqueous base material includes the water-soluble polymer of 5 to 15 mass %, the cross-linking agent of 0.02 to 5 mass %, the polyvalent alcohol of 10 to 60 mass % and water of 10 to 60 mass % relative to the total amount of the percutaneously absorbable preparation layer.

Examples of the rubber-type polymer of component 4) may include, but are not limited to, styrene-isoprene styrene block copolymer, styrene-butadiene block copolymer, polyisobutylene, crude caoutchouc, polyisoprene and polybutene. These rubber-type polymers may be used by solely one kind, or as a suitable mixture of two or more kinds. The amount of these rubber-type polymers to be incorporated is about 10 to 50 mass % relative to the total amount of the percutaneously absorbable preparation layer.

Examples of the plasticizer of component 5) may include, but are not limited to, liquid paraffin, vegetable oil, animal oil, polybutene, low molecular polyisobutylene, vaseline, lanolin and higher aliphatic esters. These plasticizers may be used by solely one kind, or as a suitable mixture of two or more kinds. The amount of these plasticizers to be incorporated is about 10 to 50 mass % relative to the total amount of the percutaneously absorbable preparation layer.

Examples of the tackifier of component 6) may include, but are not limited to, petrolatum resins, rosin-based resins, aqueous rosins, ester gum, terpene resins, modified terpene resins, aromatic hydrocarbon resins and aliphatic hydrocarbon resins. These tackifiers may be used by solely one kind, or as a suitable mixture of two or more kinds. The amount of these tackifiers to be incorporated is about 5 to 50 mass % relative to the total amount of the percutaneously absorbable preparation layer.

Preferably, the rubber-type base material includes the rubber-type polymer in an amount of 10 to 40 mass %, the plasticizer in an amount of 10 to 40 mass %, and the tackifier in an amount of 5 to 40 mass % relative to the total amount of the percutaneously absorbable preparation layer.

If necessary, the percutaneously absorbable preparation layer of the medicated patch of the present invention may include, besides the active component 5-methyl-1-phenyl-2-(1H)-pyridone or a pharmaceutically acceptable salt thereof, a dissolving agent and an aqueous or rubber-type base material, other various additives including percutaneously absorption accelerators, tackifiers, softening agents, antioxidants, antiaging agents, preserving agent, perfume materials, pH adjusting agents, emulsifying agents, dispersing agents, stabilizers, antiseptic agents and excipients, which are commonly used in conventional percutaneously absorbable preparations.

The percutaneously absorption accelerator is not specifically limited as long it is commonly used in conventional percutaneously absorbable preparations, and examples may include alcohols, aliphatic acids, aliphatic acid esters, aliphatic acid ethers, lactic acid esters, acetic acid esters, terpene compounds, pyrrolidone derivatives, organic acids, organic acid esters, essential oil, hydrocarbons, propylene carbonate and Eizon or derivatives thereof. More specifically, examples of the percutaneously absorption accelerator include ethanol, lauryl alcohol, myristyl alcohol, cetyl alcohol, crotamiton, cyclodextrin, thioglycolic acid calcium, N-methyl-2-byrrolidone, ethyl lactate, cetyl lactate, lactic acid, urea, 1-menthol, d-limonene and dl-camphor. These percutaneously absorption accelerators may be used by solely one kind, or as a suitable mixture of two or more kinds. The amount of percutaneously absorption accelerators to be incorporated is about 0.1 to 20 mass % relative to the total amount of the percutaneously absorbable preparation layer.

Examples of the tackifier may include, but are not limited to, silicone rubbers, polyisobutylene rubbers, styrene-block copolymer rubbers, acrylic rubbers and natural rubber adhesive materials. These tackifiers may be used by solely one kind, or as a suitable mixture of two or more kinds. The amount of these tackifiers to be incorporated is about 5 to 50 mass % relative to the total amount of the percutaneously absorbable preparation layer.

Examples of the softening agent may include, but are not limited to, liquid paraffin, polybutene, castor oil, cottonseed oil, palm oil, coconut oil and processed oil. These softening agents may be used by solely one kind, or as a suitable mixture of two or more kinds. The amount of these softening agents to be incorporated is about 1 to 50 mass % relative to the total amount of the percutaneously absorbable preparation layer.

Examples of the antioxidant may include, but are not limited to, ascorbic acid, palmitic acid ascorbic acid, sodium hydrogen sulfite, sodium edetate, tetrasodium edetate, dried sodium sulfite, citric acid, sodium citrate, tocopherol acetate, dl-α-tocopherol, potassium dichloroisocyanurate, dibutylhydroxytoluene, butylhydroxyanisole, soybean lecithin, sodium pyrosulfite, benzotriazole, pentaerythryl tetrakis[3-(3,5-di-t-butyl-4-hydroxyphenyl)propionate], propyl gallate and 2-mercaptobenzimidazole. These antioxidants may be used by solely one kind, or as a suitable mixture of two or more kinds. The amount of these antioxidants to be incorporated is about 0.005 to 20 mass % relative to the total amount of the percutaneously absorbable preparation layer.

Examples of the antiaging agent may include, but are not limited to, amino acids including glycine, proline, hydroxyproline, leucine, alanine, γ-aminobutyric acid and ε-aminoprone acid, vitamins including lecinol, thiamine, riboflavin, pyridoxine hydrochloride and pantothenic acid, hydroxy acids including glycolic acid, lactic acid and salicylic acid, components, extracts and essential oils derived from vegetables including tannin, flavonoid, saponin, allantoin and dog fennel, sweetroot, garden chamomile, carrot and rice. These antiaging agents may be used by solely one kind, or as a suitable mixture of two or more kinds. The amount of these antiaging agents to be incorporated is about 0.005 to 20 mass % relative to the total amount of the percutaneously absorbable preparation layer.

Examples of the preserving agent may include, but are not limited to, methyl parahydroxybenzoate, ethyl parahydroxybenzoate, propyl parahydroxybenzoate, chlorobutanol and benzyl alcohol. These preserving agents may be used by solely one kind, or as a suitable mixture of two or more kinds. The amount of these preserving agents to be incorporated is about 0.005 to 5 mass % relative to the total amount of the percutaneously absorbable preparation layer.

Examples of the perfume material may include, but are not limited to, fragrance materials including benzyl, linalyl acetate, amyl acetate, benzaldehyde, cinnamaldehyde, citronellal, menthol, citral and cis-jasmone, and medicinally active materials including methyl salicylate, camphor and cresol. These perfume materials may be used by solely one kind, or as a suitable mixture of two or more kinds. The amount of perfume materials to be incorporated is about 0.05 to 5 mass % relative to the total amount of the percutaneously absorbable preparation layer.

The pH adjusting agent is not specifically limited so long it is commonly used in conventional percutaneously absorbable preparations, and examples thereof may include inorganic acids including hydrochloric acid, sulfuric acid, nitric acid, hydrobromic acid and phosphoric acid or salts thereof, organic acids including acetic acid, succinic acid, fumaric acid, malic acid, oxalic acid, lactic acid, glutalic acid, salicylic acid and tartaric acid or salts thereof, aliphatic acids including palmitic acid, stearic acid, oleic acid and linoleic acid or salts thereof, and inorganic bases including sodium hydroxide and calcium hydroxide, and organic bases including ammonia, diisopropanolamine, diethanolamine, triethanolamine and triethylamine. These pH adjusting agents may be used by solely one kind, or as a suitable mixture of two or more kinds. The amount of these pH adjusting agents to be incorporated is about 0.05 to 10 mass % relative to the total amount of the percutaneously absorbable preparation layer.

Examples of the emulsifier may include, but are not limited to, sorbitan monooleate, polyacrylic acid, polyacrylamide, poly N-vinylpyrrolidone, chitin, chitosan and cellulose. These emulsifiers may be used by solely one kind, or as a suitable mixture of two or more kinds. The amount of these emulsifiers to be incorporated is about 0.05 to 10 mass % relative to the total amount of the percutaneously absorbable preparation layer.

The dispersing agent is not specifically limited as long as it improves the dispersibility of the components in the percutaneously absorbable preparation layer, and examples may include synthetic aluminum silicate, hydrous aluminum silicate, aluminum hydroxide, magnesium silicate, zinc oxide, titanium oxide, and metal salts of aliphatic acids including metal salts of stearic acid. These dispersing agents may be used by solely one kind, or as a suitable mixture of two or more kinds. The amount of these dispersing agents to be incorporated is about 0.5 to 50 mass % relative to the total amount of the percutaneously absorbable preparation layer.

As the stabilizer, for example, those exemplified above as pH adjusting agents may be used. Furthermore, as the stabilizer, sodium hydrogen sulfite, ascorbic acid, sodium ascorbate, butylhydroxyanisole, dibutylhydroxytoluene, propyl gallate, tocoferol acetate and D-α-tocoferol may be used. These stabilizers may be used by solely one kind, or as a suitable mixture of two or more kinds. The amount of these stabilizers to be incorporated is about 0.005 to 20 mass % relative to the total amount of the percutaneously absorbable preparation layer.

Examples of the antiseptic agent may include, but are not limited to, methylparaben, ethylparaben, propylparaben, butylparaben and phenoxyethanol. These antiseptic agents may be used by solely one kind, or as a suitable mixture of two or more kinds. The amount of these antiseptic agents to be incorporated is about 0.005 to 5 mass % relative to the total amount of the percutaneously absorbable preparation layer.

Examples of the excipient may include, but are not limited to, sugars including glucose, fructose, galactose, mannose, palatinose, sucrose, maltose, lactose, trehalose, oligo sucrose and dextrin, and celluloses including crystalline cellulose, methyl cellulose, carboxymethyl cellulose or salts thereof, hydroxypropyl cellulose and hydroxypropyl methyl cellulose. These excipients may be used by solely one kind, or as a suitable mixture of two or more kinds. The amount of these excipients to be incorporated is about 0.1 to 40 mass % relative to the total amount of the percutaneously absorbable preparation layer.

The medicated patch of the present invention may be in the form of various medicated patches including cataplasms, plasters and tapes according to the purpose. The medicated patch of the present invention may be prepared, for example, by applying an aqueous base material or a rubber-type base material in which 5-methyl-1-phenyl-2-(1H)-pyridone and the dissolving agent have been added in predetermined amounts (percutaneously absorbable preparation) on a suitable substrate by a predetermined thickness to form a percutaneously absorbable preparation layer, coating the layer with a predetermined liner, and cutting into a desired size. Alternatively, the medicated patch of the present invention may be formed, depending on the production method, for example, by first applying the base material including 5-methyl-1-phenyl-2-(1H)-pyridone and the dissolving agent (percutaneously absorbable preparation) on a liner to form a percutaneously absorbable preparation layer, coating the layer with a substrate to transfer the percutaneously absorbable preparation layer on the substrate.

Furthermore, since the medicated patch of the present invention is directly contacted to an affected area, it is preferable to product the medicated patch as mentioned above and subject it to sterilization treatment. Although the sterilization method is not specifically limited as long as it is a commonly used method in sterilization of conventional drugs, for example, γ-ray sterilization method, electron beam sterilization method, high pressure vapor sterilization method, ethylene oxide gas sterilization method or the like is used.

The substrate used in the medicated patch of the present invention is not specifically limited, and a material commonly used as a substrate for medicated patches may be used. As these substrates, for example, woven fabric, nonwoven fabric, sheets, films or laminates thereof of natural or synthetic polymers, preferably vinyl chloride films, polyethylene films, ethylene copolymer films, polypropylene films, polyurethane, as well as woven fabric and nonwoven fabric, and laminates of these and plastics are used.

The size, form, thickness and the like of these substrates are suitably selected.

The liner used in the medicated patch of the present invention is not specifically limited, and a material commonly used as a liner for medicated patches may be used. Examples of these liners may include sheets, films of natural or synthetic polymers, or laminates thereof, preferably, sheets and films of release paper which has been subjected to treatment to make releasing easy (e.g., coating with a synthetic polymer), cellophane, polyethylene, polyethylene terephthalate, polybropylene, polyester, polyvinylidene chloride and the like, or laminates thereof.

Hereinafter, the usefulness of the present invention will be described with referring to Examples and Test Examples, but the present invention is not limited by these. Unless otherwise mentioned, the part is based on mass.

EXAMPLES

Example 1

Sodium polyacrylate (5 parts), acrylic acid starch (2.5 parts), carboxymethylcellulose sodium (1 part) and concentrated glycerin (30 parts) were mixed (liquid A). 5-Methyl-1-phenyl-2-(1H)-pyridone (2 parts or 3 parts) as an active component and tartaric acid (1 part) and water (54.13 parts or 53.16 parts) were mixed (liquid B). Peppermint oil (1 part, dissolving agent) was dissolved in a surfactant (0.3 part) (liquid C). Liquids B and C were added to liquid A, and a polyacrylic acid copolymerized emulsion (3 parts) and an aluminum hydroxide gel (0.04 part) were added and stirred evenly. This mixture (percutaneously absorbable preparation) was flatted on a polyethylene film (liner) to form a percutaneously absorbable preparation layer, and the layer was coated with polyester nonwoven fabric (substrate). This was cut into a desired size to give a medicated patch of Example 1 including 5-methyl-1-phenyl-2-(1H)-pyridone by 2% or 3%.

Example 2

Polyisobutylene (10 parts), a styrene-isoprene-styrene block copolymer (25 parts), dibutylhydroxytoluene (0.5 part), liquid paraffin (39.5 parts), a petrolatum resin (17 parts) were mixed at 140° C. (liquid A). 5-methyl-1-phenyl-2-(1H)-pyridone (3 parts) as an active component was evenly mixed into propylene glycol (5 parts) (dissolving agent). Liquid A was heated to 120° C., and liquid B was added to liquid A and mixed. This mixture (percutaneously absorbable preparation) was flatted on polyester nonwoven fabric (substrate) to form a percutaneously absorbable preparation layer, which was coated with a polyester film (liner), cooled to room temperature and then cut into a desired size to give a medicated patch of Example 2 including 5-methyl-1-phenyl-2-(1H)-pyridone by 3%.

Test Example 1

In Vitro Skin Permeability Test

1) Test method

Under sodium pentobarbital anesthesia, the abdomen of a male Wistar rat (7-week old) was shaved, the skin was excised, and the lipid on the dermis of the skin was carefully removed. The skin was adhered the dermis-side down on a vertical diffusion cell in which water at 37° C. had been circulated in advance, and the 2%-medicated patch produced in Example 1, which was punched out by a diameter of 1 cm, was adhered on the center portion of the skin and fixed by clipping with a dome-shaped cell. The receiver liquid, which had been warmed in an isothermal bath at 37° C., was then put into the dermis-side, an L-shaped tube was attached to a sampling port and fixed, and a certain amount of receiver solution was further added. The receiver solution was stirred with a magnetic stirrer, a certain amount of receiver solution was taken over time, and the same amount of receiver solution was supplied. The amount of the active component (5-methyl-1-phenyl-2-(1H)-pyridone) in the collected sample was quantified by high-performance liquid chromatography (HPLC) using the following conditions to calculate the accumulated skin permeation amount and skin permeation rate of 5-methyl-1-phenyl-2-(1H)-pyridone. The results are shown in FIGS. 1 and 2, respectively.

<HPLC Conditions>
Column: CAPCELL PAK $C_{18}$ 5 μm 4.6×150 mm
Column temperature: 40° C.
Flow rate: 1 mL/min
Detection wavelength: 318 nm
Injection amount: 10 μL
Mobile phase: acetonitrile:methanol:50 mM phosphate buffer (pH 2.7)=225:100:675 (9:4:27)

2) Results (1) Accumulated skin permeation amount of 5-methyl-1-phenyl-2-(1H)-pyridone As shown in FIG. 1, at 12 hours after adhesion to the skin, only about 20% of the active component (5-methyl-1-phenyl-2-(1H)-pyridone) remained in the medicated patch of Example 1. In other word, about 90% of the active component in total was released to (permeated) the skin from the medicated patch of Example 1 over 24 hours.

From this fact, it was found that the medicated patch including 5-methyl-1-phenyl-2-(1H)-pyridone of the present invention was excellent in skin permeability of the active component and sustentation of its medicinal effect.

(2) Skin permeation rate of 5-methyl-1-phenyl-2-(1H)-pyridone

As shown in FIG. 2, the skin permeation rate of the active component (5-methyl-1-phenyl-2-(1H)-pyridone) of the medicated patch of Example 1 was as very fast as 0.1 mg/cm$^2$/h or more within 3 hours after adhesion to the skin.

From this fact, it was found that the medicated patch including 5-methyl-1-phenyl-2-(1H)-pyridone of the present invention was excellent in immediate effectivity.

Test Example 2

Treatment Test on Hypertrophic Scar

1) Test Method

Swine (18-week old/Duroc strain/sexuality female) in which hypertrophic scar had been formed by cutting at a swinery were divided into three groups including a control group, a base material group and a 3%-medicated patch group. The medicated patch of Example 1 and a medicated patch which was similar to Example 1 except that 5-methyl- 1-phenyl-2-(1H)-pyridone was removed from the percutaneously absorbable preparation layer were each adhered on the hypertrophic scar site of the swine in the 3%-medicated patch group and the base material group once a day for 24 hours, from 25 days after formation of the incised wound.

After 9 weeks, the thickness of the isolated skin (scared skin) on the hypertrophic scar site and the thickness of the normal isolated skin of the swine in each group were measured using a digital scale.

A static analysis was performed by Dunnett's multiple comparison test for the obtained thicknesses of the scared skin and normal skin of the swine in the three groups. The results are shown in FIG. 3.

In FIG. 3, ** represents $p<0.01$ (vs. control group).

2) Results

As shown in FIG. 3, in the group of the medicated patch to which the medicated patch of the present invention including 5-methyl-1-phenyl-2-(1H)-pyridone and the dissolving agent in combination in the percutaneously absorbable preparation layer was used, the thickness of the scared skin was decreased (recovered) to about the thickness of the normal skin, whereas the thickness of the scared skin was decreased little in the base material group in which the percutaneously absorbable preparation layer did not include the combination.

From the above-mentioned result, it was found that the medicated patch including 5-methyl-1-phenyl-2-(1H)-pyridone of the present invention was effective in the prophylaxis and treatment of hypertrophic scars using swine as models.

Since such result could be obtained in the skin of swine, which have a similar skin structure to that of humans, the medicated patch including 5-methyl-1-phenyl-2-(1H)-pyridone of the present invention may be considered to be similarly effective for the prophylaxis and treatment of hypertrophic scars in humans.

Furthermore, from the result of the above-mentioned hypertrophic scar test, the medicated patch including 5-methyl-1-phenyl-2-(1H)-pyridone of the present invention may be considered to be similarly effective for the prophylaxis and treatment of other skin diseases such as keloid, contact dermatitis, infectious verruca (wart), pustulosis palmaris et plantaris or fibrous skin disease to which 5-methyl-1-phenyl-2 (1H)-pyridone is effective as a treatment drug.

Figure 1:
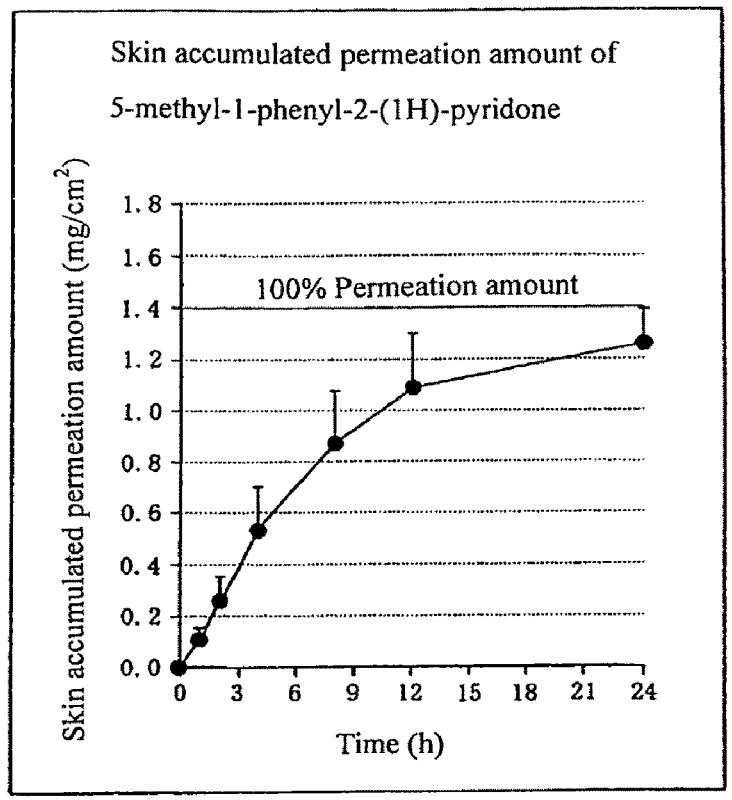
FIG. 1 is a graph showing the relationship between the lapse time after adhesion of a medicated patch including 5-methyl-1-phenyl-2-(1H)-pyridone of Example 1 on the skin of a rat and an accumulated permeation amount of 5-methyl-1-phenyl-2-(1H)-pyridone.
Figure 2:
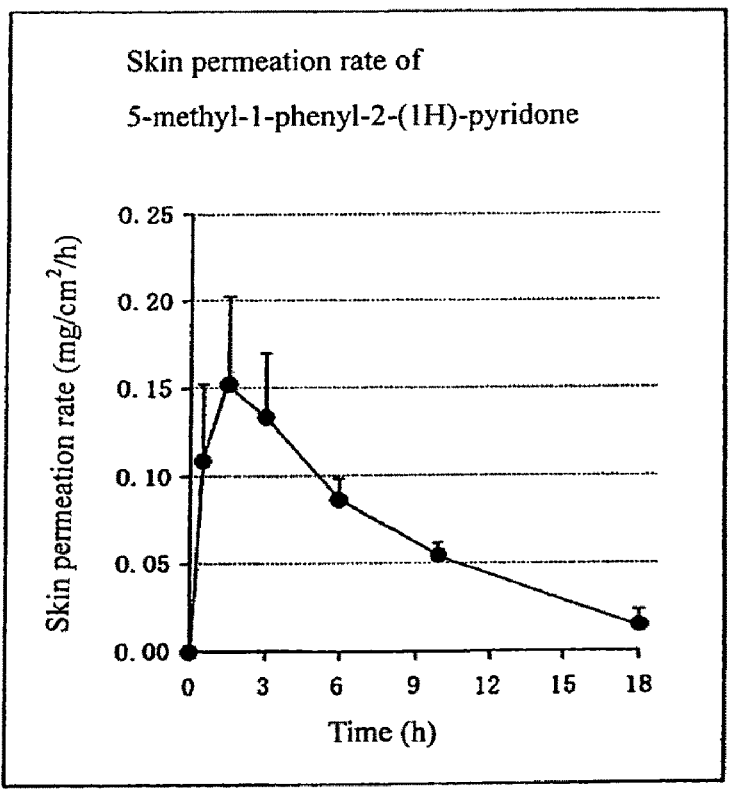
FIG. 2 is a graph showing the relationship between the lapse time after adhesion of the medicated patch including 5-methyl-1-phenyl-2-(1H)-pyridone of Example 1 on the skin of the rat and a skin permeation rate.
Figure 3:
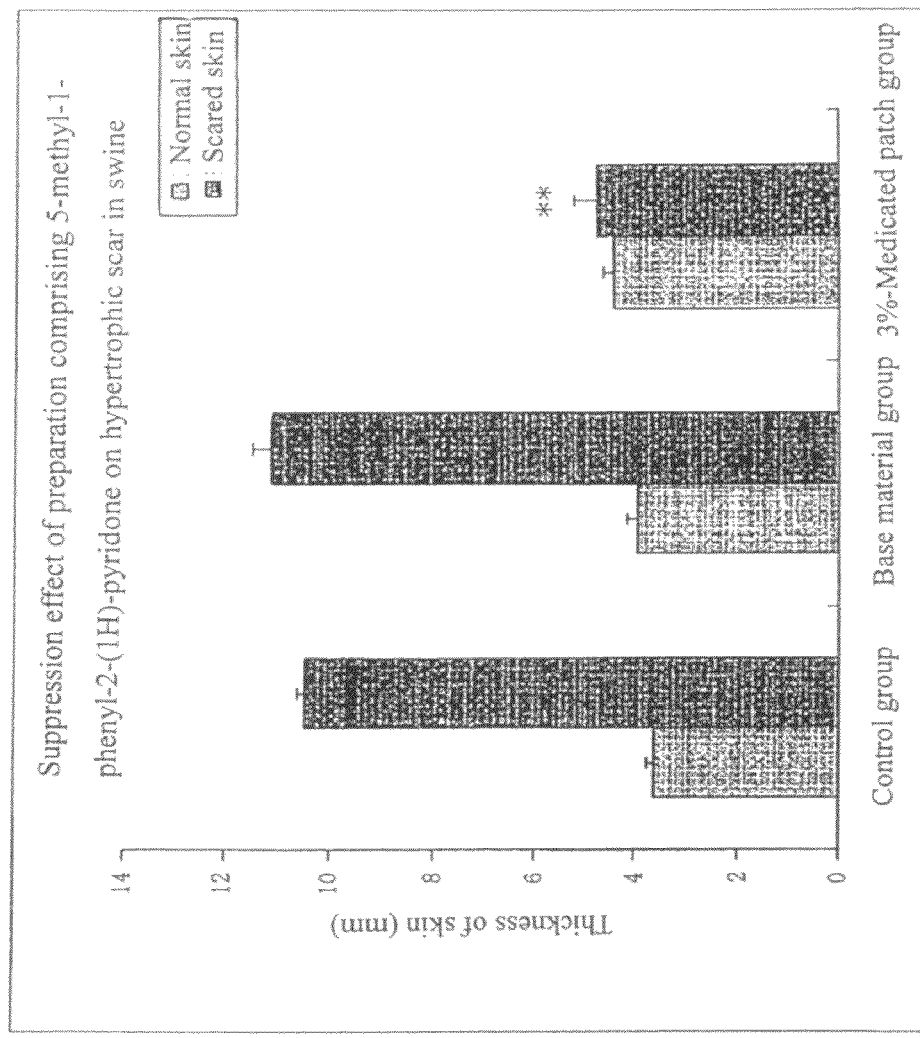
FIG. 3 is a graph showing the result of the hypertrophic scar suppression test in swine in Test Example 2.

The invention claimed is:

1. A medicated patch comprising a percutaneously absorbable preparation layer, the percutaneously absorbable preparation layer comprising:

5 methyl-1-phenyl-2-(1H)-pyridone or a pharmaceutically acceptable salt thereof as an active component, a dissolving agent, and an aqueous base material, wherein the aqueous base material comprises a water-soluble polymer in an amount of 1 to 20 mass %, a cross-linking agent in an amount of 0.01 to 20 mass %, the cross-linking agent being a salt which generates a bivalent or trivalent metal ion, a polyvalent alcohol in an amount of 10 to 80 mass % and water in an amount of 5 to 80 mass % relative to a total amount of the percutaneously absorbable preparation layer, and the active component is contained in an amount of 0.1 to 30 mass % relative to the total amount of the percutaneously absorbable preparation layer.

2. The medicated patch according to claim 1, wherein the dissolving agent is selected from the group consisting of peppermint oil, oleyl alcohol, isopropanol, propylene glycol, butylene glycol, N-methyl-pyrrolidone, diethylene glycol monoethyl ether, triacetine, glycerin, crotamiton, macrogol, isopropyl myristate, glycerin triethyl hexanoate, diisopropyl sebacate, diethyl sebacate, diisopropyl adipate, triethyl citrate, ethylene glycol salicylate, propylene carbonate and medium-chain fatty acid triglycerides.

3. A medicated patch comprising a percutaneously absorbable preparation layer, the percutaneously absorbable preparation layer comprising:

5 methyl-1-phenyl-2-(1H)-pyridone or a pharmaceutically acceptable salt thereof as an active component, a dissolving agent, and a rubber-type base material, and wherein the rubber-type base material comprises a rubber-type polymer in an amount of 10 to 50 mass %, a plasticizer in an amount of 10 to 50 mass % and a tackifier in an amount of 5 to 50 mass % relative to a total amount of the percutaneously absorbable preparation layer, and the active component is contained in an amount of 0.1 to 30 mass % relative to the total amount of the percutaneously absorbable preparation layer.

4. The medicated patch according to claim 3, wherein the dissolving agent is selected from the group consisting of peppermint oil, oleyl alcohol, isopropanol, propylene glycol, butylene glycol, N-methyl-pyrrolidone, diethylene glycol monoethyl ether, triacetine, glycerin, crotamiton and macrogol, isopropyl myristate, glycerin triethyl hexanoate, diisopropyl sebacate, diethyl sebacate, diisopropyl adipate, triethyl citrate, ethylene glycol salicylate and propylene carbonate.

5. The medicated patch according to claim 3, wherein the active component is contained in an amount of 0.5 to 20 mass % relative to the total amount of the percutaneously absorbable preparation layer.

6. The medicated patch according to claim 3, wherein the active component is contained in an amount of 0.5 to 10 mass % relative to the total amount of the percutaneously absorbable layer.

* * * * *